United States Patent [19]

Wardlaw

[11] 4,378,015

[45] Mar. 29, 1983

[54] AUTOMATIC INJECTING SYRINGE

[76] Inventor: Stephen C. Wardlaw, 128 Sunset Hill Dr., Branford, Conn. 06405

[21] Appl. No.: 332,976

[22] Filed: Dec. 21, 1981

[51] Int. Cl.³ .............................................. A61M 5/00
[52] U.S. Cl. ......................... 128/218 F; 128/218 DA
[58] Field of Search ........... 128/218 F, 218 A, 218 D, 128/218 DA, 215, 216, 220

[56] References Cited

U.S. PATENT DOCUMENTS

| | | | |
|---|---|---|---|
| 3,094,989 | 6/1963 | Stauffer | 128/218 F |
| 3,702,609 | 11/1972 | Steiner | 128/218 F |
| 4,227,528 | 10/1980 | Wardlaw | 128/218 A |
| 4,258,713 | 3/1981 | Wardlaw | 128/218 F |

*Primary Examiner*—John D. Yasko
*Attorney, Agent, or Firm*—William W. Jones

[57] ABSTRACT

The hypodermic syringe of this invention is of simplified construction and employs a retracted needle contained within a housing, which needle is driven to inject a dose of medication by pressing the housing against the patient's skin. The syringe has a minimum of parts and may be easily and inexpensively assembled. A safety feature is included which prevents accidental operation of the syringe.

5 Claims, 6 Drawing Figures

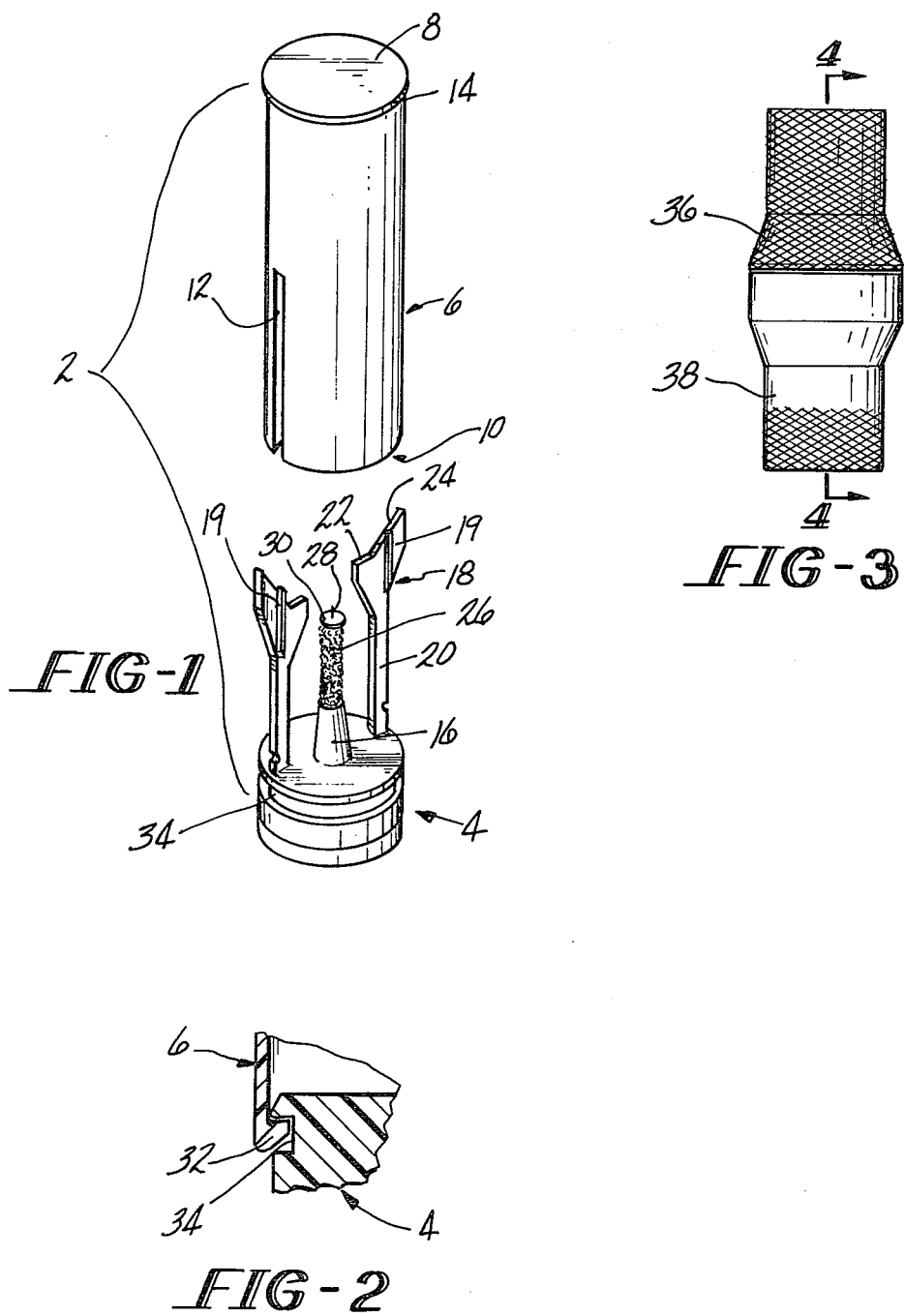

AUTOMATIC INJECTING SYRINGE

This invention relates to an improved disposable automatic injecting syringe of the general type disclosed in my issued U.S. Pat. Nos. 4,188,950; 4,196,732; 4,227,528; and 4,258,713. More specifically, this invention relates to an improved automatic syringe of simplified construction, which can be easily assembled and easily operated.

The syringe of this invention is of the general type having a housing in which a cannula or needle is retractedly disposed, the needle being driven outwardly of the housing in order to deliver an injection of medication. A movable ampoule is disposed in the housing, the ampoule serving to contain the medication, and also serving as an intermediate to driven the needle to the injecting position. This general type of syringe is shown in U.S. Pat. Nos. 2,866,458; 2,871,856; 3,066,670; 3,136,313; 3,320,955; 3,403,679; 3,572,336; 3,702,609; 3,712,301; 3,797,489; 3,882,863; 3,943,927; 3,977,402; 4,031,889; and others. As a general matter, the syringes disclosed in the above-noted patents are of relatively complicated construction, and are relatively expensive to manufacture and assemble. The syringe of this invention is constructed of relatively few parts and easily manufactured and assembled. The construction of the syringe of this invention also provides for a more compact unit than found in the prior art.

The syringe of this invention includes: a pump-type ampoule; an ampoule holder; an operating spring; a two-piece housing comprising an upper portion and a base; a needle and needle holder; a needle bender; and an outer two-piece cover, one portion of which serves as an actuator for the device when the latter is pressed against a patient's skin. The other portion of the cover serves as a safety which prevents operation of the syringe unless removed from the housing. The device can be gas sterilized after assembly, and then the cover can be sealed for storage until the device is needed for use.

It is, therefore, an object of this invention to provide a disposable hypodermic syringe, of the retracted needle type, which is formed from a minimum number of parts and which can be easily and inexpensively assembled.

It is an additional object of this invention to provide a syringe of the character described which is operated by being pressed against the patient's skin.

It is a further object of this invention to provide a syringe of the character described which includes a two-piece cover, one part of which serves as an actuator for the syringe and the other part of which serves as a safety for the syringe.

These and other objects and advantages of the invention will become more readily apparent from the following detailed description of a preferred embodiment thereof, when taken in conjunction with the accompanying drawings, in which:

FIG. 1 is an exploded view of the two-piece housing and needle holder preferred for use in the syringe of this invention;

FIG. 2 is a fragmented cross-sectional view of a portion of the syringe showing the joint preferred for use between the two component pieces of the syringe housing;

FIG. 3 is a side elevation view of a preferred embodiment of the syringe of this invention shown assembled and in its outer two-piece cover;

Figure 4:
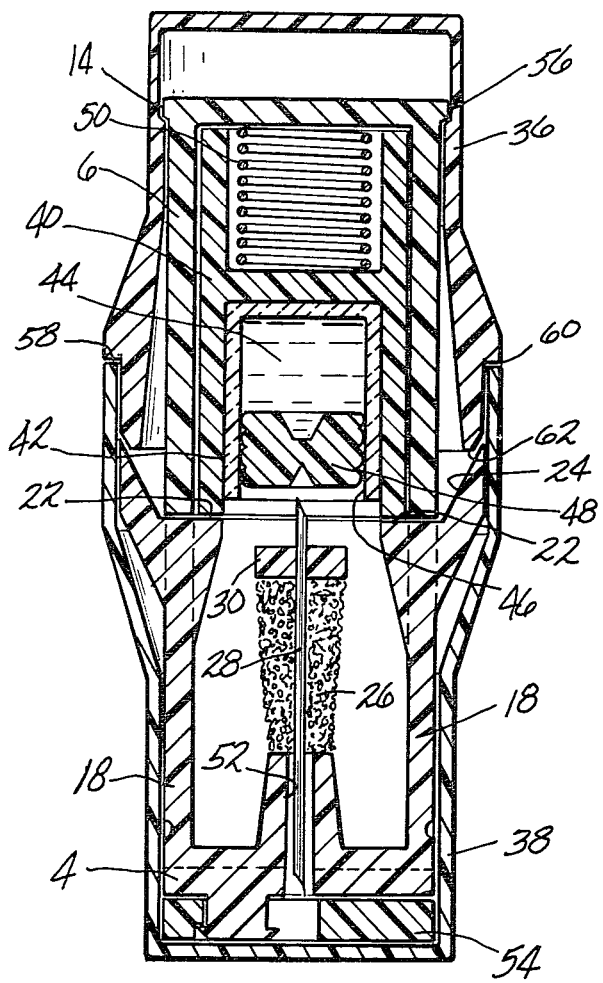
FIG. 4 is a sectional view of the assembled syringe taken along line 4—4 of FIG. 3.

Referring now to the drawings, there is shown in FIG. 1 a preferred embodiment of a syringe, denoted generally by the numeral 2. The syringe 2 includes a housing formed of two parts, namely, a base part 4, and a top part 6. The top part 6 is hollow and includes a closed end portion 8 and an open end portion 10. A pair of slots 12 disposed 180° apart from each other extend through the side wall of the top part 6 and through to the open end 10 of the top part 6. A radially enlarged rib 14 is formed on the side wall of the top part 6 adjacent to the closed end portion 8 thereof.

The base part 4 of the housing is formed with an axially projecting pedestal 16 and a pair of 180° offset elongated dogs 18. Each of the dogs 18 includes a resilient stem portion 20, a support portion 22, a cam portion 24 and a pair of ribs 19 to prevent the dogs from being drawn into the unit during assembly. On the pedestal 16, there is disposed a crushable foam columnar needle holder 26 through which extends the needle or cannula 28. A ferrule 30 is attached to the needle 28 adjacent to its upper end. The top part 6 is attached to the base part 4 by means of a snap fit with an internal rib 32 formed about the open end 10 of the top part snapping into a circumferential groove 34 formed in the side wall of the base part 4 (see FIG. 2). When thus assembled, the dogs 18 are disposed in the slots 12 of the top part 6.

The fully assembled syringe includes an outer cover having a first part 36 which serves as a syringe actuator, and a second part 38 which serves to prevent accidental actuation of the syringe (see FIG. 3). The operation of the cover parts 36 and 38 is more fully disclosed hereinafter.

Referring now to FIG. 4, the internal construction of the syringe is more fully disclosed. In the top housing part 6, there is slidably disposed an ampoule carrier 40. The ampoule carrier 40 contains an ampoule 42 which is filled with a dose of a medicament 44. The ampoule 42 includes an open end 46 which is closed by an elastomeric piston 48. A coil spring 50 biases the ampoule carrier 40 and ampoule 42 toward the base part 4 of the housing; however, baseward movement of the ampoule carrier 40 is prevented by the support portions 22 of the dogs 18. It will be noted that the pedestal 16 is provided with a through bore 52 into which the needle 28 extends. The foam column 26 supports the needle 28 and properly positions it on the pedestal 16. The ferrule 30 secured to the needle 28 controls the depth to which the needle will puncture the piston 48 and enter the medicament dose 44 when the device is used. Mounted on the outer lower end surface of the base part 4 of the housing is a needle retracting and bending disk 54. The operation of this disk 54 is disclosed in the aforementioned U.S. Pat. No. 4,188,950, the disclosure of which is specifically incorporated hereinto by reference.

The two-part outer cover, including the actuator 36 and the safety 38, is mounted on the housing 2 to completely enclose the latter. The interior of the actuator 36 is undercut at 56 so as to form an interference fit with the rib 14 on the top housing part 6 so that the actuator 36 can slidably reciprocate over the top housing part 6 but will not accidentally become disconnected therefrom. It is noted that the upper end surface 58 of the safety 38 engages an annular flange 60 on the actuator 36 to properly position the latter on the housing. After the assembly is sterilized, the joint between the actuator 36 and safety 38 is sealed with tape, wax, a weld securement, or the like, so as to maintain the internal sterility thereof and secure the two parts of the outer cover together.

When the syringe is properly assembled, the lower end 62 of the actuator is closely adjacent to the cam surfaces 24 on the dogs 18. Premature engagement between the actuator 36 and dogs 18 is prevented, however, by the surfaces 58 and 60 on the safety 38 and actuator 36, respectively. Furthermore, outward deflection of the dogs 18 is resisted by the overlying side wall of the safety 38. Thus, the device can be safely stored and carried about in its cocked condition without the risk of accidental actuation.

Assembly of the device is accomplished as follows: The filled ampoule 42 and carrier 40 are first inserted into the top 6 of the housing 2 along with the spring 50. This assembly is then pressed over the lower assembly which consists of the base 4, needle 28 and needle ferrule 30, and the crushable needle-holding foam column 26. This assembly operation compresses the spring 50 and cocks the unit. This assembly step is completed when the rib 32 on the top part 6 snaps into engagement with the groove 34 on the base part 4, which locks the two parts together. The safety part 38 of the outer cover is then placed over the assembled housing and the actuator part 36 is then pressed down onto the upper half of the assembled housing until the rib 14 passes the undercut 56. The syringe is thus assembled and can then be gas sterilized prior to sealing the two parts of the outer cover together.

Figure 5:
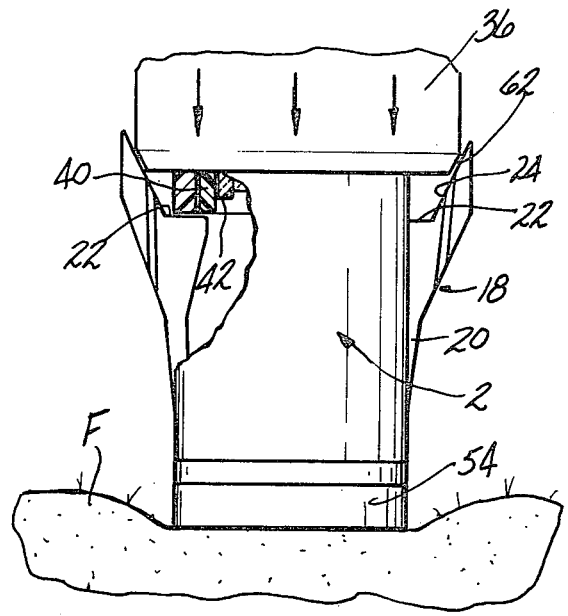
FIG. 5 is a fragmented side elevational view, taken partly in section, showing how the ampoule is released to be driven by the spring.
Figure 6:
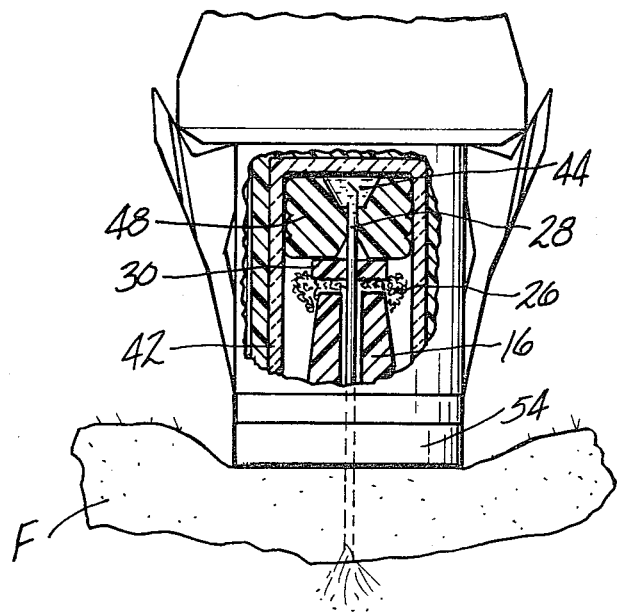
FIG. 6 is a fragmented side elevational view, partly in section, showing how the injection is administered by the device.

FIGS. 5 and 6 illustrate the manner of operation of the syringe. To operate the syringe, the seal between the actuator 36 and the safety 38 is broken, and the safety 38 is pulled away from the actuator 36 and off of the housing 2. The bottom surface of the disk 54 is then pressed against the patient's flesh F and the actuator 36 is pressed down toward the patient's flesh. The downward movement of the actuator 36 over the housing 2 moves the lower end surface 62 of the actuator 36 against the cam surfaces 24 on the dogs 18 causing the dogs 18 to deflect radially outwardly by reason of their resilient stem portions 20. This outward deflection moves the support portions 22 of the dogs 18 out from under the ampoule carrier 40 and allows the spring to drive the ampoule carrier 40 and ampoule 42 down toward the needle 28. The needle 28 then punctures the piston 48 and enters the medicament 44. The outer surface of the piston 48 engages the ferrule 30 and drives the needle 28 into the flesh of the user, the foam column 26 being crushed during driving of the needle 28. The pedestal 16 stops the driving of the needle 28 and operates through the ferrule 30 to push the piston 48 into the ampoule 42 thereby causing the medicament 44 to be pumped through the needle 28 into the flesh F of the user. After the injection has been administered, the needle 28 is withdrawn from the user's flesh and the disk 54 is twisted to retract and bend the needle 54 to render the syringe and needle inoperative for further use.

To aid in determining whether the syringe has been successfully fired, the housing 2 and the cover parts 36 and 38 can be made of transparent plastic. This will allow the contents of the syringe to be inspected visually after assembly.

It will be readily appreciated that the syringe of this invention is of simplified construction, having only two housing parts and two cover parts, all of which can be easily molded from plastic using simple mold configurations. Notwithstanding the minimum number of parts, the device is easily operated, and provides reliable safety features which protect against accidental operation. The syringe is quite compact, particularly with respect to its longitudinal dimension, and can be easily packed, stored, and carried about by a user. Sterilization is assured until usage is necessary, even when carried about by a user.

It is understood that the above constitutes a description of a preferred embodiment of the invention and that the scope of the invention is not to be limited otherwise than as required by the appended claims.

What is claimed is:

1. An automatic hypodermic syringe comprising:
   (a) a housing including a base member and a top member interconnected to form said housing;
   (b) ampoule means containing a dose of a medicament, said ampoule means being mounted in said housing for movement therein between a cocked position and a driven position;
   (c) spring means in said housing for driving said ampoule means from said cocked position to said driven position;
   (d) a hypodermic needle mounted in said housing in a recessed position completely contained within said housing, said needle being movable to an injecting position protruding from said housing responsive to movement of said ampoule means to said driven position, and said needle being operable to pierce said ampoule means and deliver an injection of said medicament when in said injecting position;
   (e) catch means on said base member for engagement with said ampoule means for releasably retaining said ampoule means in said cocked position;
   (f) safety means outwardly overlying said base member and said catch means, said safety means being operable to retain said catch means in retaining engagement with said ampoule means; and
   (g) actuating means outwardly overlying said top member and movably mounted thereon, said actuating means being operable, upon removal of said safety means from said base member, to move toward said base member, to engage said catch means and move the latter out of retaining engagement with said ampoule means whereby the latter is moved from said cocked position to said driven position.

2. The syringe of claim 1, wherein said safety means and said actuating means are releasably joined together to form a sealed, sterile container for said housing.

3. An automatic hypodermic syringe comprising:
   (a) a housing including a base member and a top member interconnected to form said housing, said base member including integral catch means having a support portion and a cam portion, said catch means extending from said base member into said top member;
   (b) ampoule means containing a dose of a medicament, said ampoule means being mounted in said top member for movement between a cocked position and a driven position, and said ampoule means being releasably retained in said cocked position by engagement with said support portion of said catch means;

(c) spring means disposed in said top member in engagement with said ampoule means to bias the latter against said catch means and toward said driven position;

(d) a hypodermic needle mounted in said housing in a recessed position completely contained within said housing, said needle being movable to an injecting position protruding from said housing responsive to movement of said ampoule means to said driven position, and said needle being operable to pierce said ampoule means and deliver an injection of said medicament when in said injecting position;

(e) safety means outwardly overlying said base member and said catch means, said safety means being operable to retain said catch means in supporting engagement with said ampoule means; and (f) actuating means outwardly overlying said top member and movably mounted thereon, said actuating means being operable to engage said cam portion of said catch means and move the latter out of retaining engagement with said ampoule means whereby the latter is moved from said cocked position to said driven position, said safety means and said actuating means being juxtaposed and releasably sealed together to form a sealed sterile container for said housing.

4. An automatic hypodermic syringe comprising:

(a) a housing including a base member and a top member interconnected to form said housing, said top member including longitudinally extending slots formed in a side wall of said top member, said base member including a plurality of integral elongated catch means formed thereon, said catch means extending into said slots in said top member, each of said catch means including a support portion extending radially inwardly into the interior of said top member;

(b) ampoule means containing a dose of a medicament, said ampoule means being mounted in said top member for movement therein between a cocked position and a driven position, said ampoule means being releasably retained in said cocked position by engagement with said support portions of said catch means;

(c) spring means disposed in said top member in engagement with said ampoule means to bias the latter against said support portions of said catch means and toward said driven position;

(d) a hypodermic needle mounted in said housing in a recessed position completely contained within said housing, said needle beinng movable to an injecting position protruding from said housing responsive to movement of said ampoule means to said driven position, and said needle being operable to pierce said ampoule means and deliver an injection of said medicament when in said injecting position;

(e) safety means outwardly overlying said base member and said catch means to retain said catch means in supporting engagement with said ampoule means; and (f) actuating means outwardly overlying said top member and movably mounted thereon, said actuating means being operable to engage said catch means, after removal of said safety means, and move said catch means out of supporting engagement with said ampoule means whereby the latter is moved to said driven position by said spring means, said safety means and said actuating means being juxtaposed and releasably sealed together to form a sealed sterile container for said housing.

5. The hypodermic syringe of claim 4, wherein said base member includes a circumferential groove, and said top member includes an inwardly extending circumferential rib snap fitted into said groove to secure said top member to said base member.

* * * * *